SELECTIVE HERBICIDAL ACTIVITY OF FLUOROAMINOPYRIDAZINES

SUMMARY OF THE INVENTION

This invention relates to the use of fluoroaminopyridazines as selective preemergence and postemergence herbicides. The fluoroaminopyridazines utilized in this invention are those of the formula

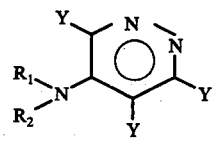

wherein each Y is a chlorine atom or a fluorine atom, preferably at least one Y being a fluorine atom and $R_1$ and $R_2$ are independently a hydrogen atom, a ($C_1$–$C_4$) alkyl group, a ($C_1$–$C_4$) haloalkyl group, a ($C_1$–$C_5$) alkynyl group a ($C_1$–$C_4$) alkanoyl group, a ($C_1$–$C_4$) haloalkanoyl group, a ($C_7$–$C_{11}$) benzoyl group, a benzyl group or a phenyl group. In a preferred embodiment of this invention Y is a fluorine atom and $R_1$ and $R_2$ are independently a hydrogen atom, a ($C_1$–$C_4$) alkyl group or a ($C_1$–$C_4$) haloalkyl group.

The most preferred embodiment of this invention is the compound 4-amino-3,5,6-trifluoropyridazine and its use as a selective preemergence or postemergence herbicide.

The compounds utilized in this invention can be prepared by general synthetic routes, one of which is described below.

One method of preparation involves reacting 3,4-dichloromaleic anhydride at elevated temperatures of from about 80° to about 120° C. with hydrazine hydrate in an appropriate solvent such as acetic acid, propionic, acid and the like to form 4,5-dichloro-3,6-dihydroxypyridazine (Formula II).

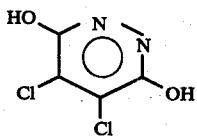

Chlorination of the 4,5-dichloro-3,6-dihydroxypyridazine with phosphorous oxychloride in an appropriate solvent such as pyridine, α-picoline, 2,6-lutidine, N,N-dimethylamine and the like at temperatures of from about 80° to about 110° C. gives the tetrachloropyridazine (Formula III).

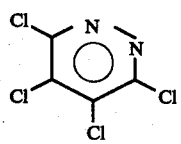

The halogen exchange of tetrachloropyridazine with an excess of potassium fluoride can be performed by maintaining the reagents at temperatures of from about 100° to 400° C. for periods of from about 1 to about 72 hours either neat or in an appropriate solvent such as dimethylsulfoxide, sulfolane, N-methylpyrrolidone, and the like to afford tetrafluoropyridazine (Formula IV).

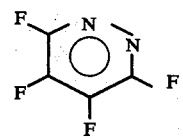

The nucleophilic substitution of a halogen atom in the 4 position of the pyridazine ring can be achieved by reacting the tetrahalopyridazine with ammonia, an alkyl, an alkynyl or an aralkylamine or an aniline at temperatures of from about 10° to about 50° C. in solvents such as methanol, ethanol, toluene, benzene, glyme, dioxane, tetrahydrofuran, diethyl ether and the like to give the product of Formula V.

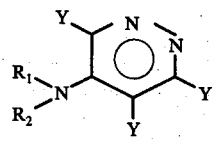

The N-acyl derivatives can be prepared by reacting an aminotrihalopyridazine of Formula V with an acyl halide in the presence of a base such as sodium hydride, n-butyllithium, potassium tert-butoxide and the like in a solvent such as glyme, benzene, tetrahydrofuran, 1,4-dioxane, toluene or combinations thereof at temperatures of from about 0 to about 100° C. for periods of from about 2 to about 24 hours.

Typical fluoroaminopyridazines which can be utilized in this invention include:
 4-amino-3,5,6-trifluoropyridazine
 4-amino-3,5-dichloro-6-fluoropyridazine
 3,5,6-trifluoro-4-methylaminopyridazine
 4-diethylamino-3,5,6-trifluoropyridazine
 5,6-dichloro-3-fluoro-4-n-propylaminopyridazine
 4-chloroacetylamino-3,5,6-trichloropyridazine
 4-benzoylamino-3,5,6-trifluoropyridazine
 3,5,6-trifluoro-4-dimethylaminopyridazine
 4-dimethylamino-3,5,6-trifluoropyridazine
 4-benzylamino-3,5,6-trifluoropyridazine
 4-amino-3,6-dichloro-5-fluoropyridazine
 4-amino-6-chloro-3,5-difluoropyridazine
 4-(1,1-dimethylpropynyl)amino-3,5,6-trichloropyridazine
 3-chloro-5,6-difluoro-4-methylaminopyridazine Table I below gives the melting point and elemental analysis of some of the compounds that can be utilized in this invention. This data is not to be construed as a limitation of the embodiment of this invention but as an exemplification of the compounds which may be so utilized.

United States Patent [19]

Yih et al.

[11] 4,083,713
[45] Apr. 11, 1978

[54] SELECTIVE HERBICIDAL ACTIVITY OF FLUOROAMINOPYRIDAZINES

[75] Inventors: Roy Y. Yih, Doylestown; Wayne O. Johnson, Warminster; Gerald E. Kollman, Chalfont, all of Pa.

[73] Assignee: Rohm and Haas Company, Philadelphia, Pa.

[21] Appl. No.: 558,568

[22] Filed: Mar. 14, 1975

[51] Int. Cl.² ............................................. A01N 9/22
[52] U.S. Cl. ........................................................ 71/92
[58] Field of Search .............................................. 71/92

[56] References Cited
U.S. PATENT DOCUMENTS

| | | | |
|---|---|---|---|
| 3,193,553 | 7/1964 | Reicheneder et al. | 71/92 X |
| 3,210,353 | 10/1965 | Reicheneder et al. | 71/92 X |
| 3,427,146 | 2/1969 | Tamura | 71/76 |
| 3,539,332 | 11/1970 | Geronimo | 71/92 |
| 3,637,691 | 1/1972 | Bublitz | 71/92 X |
| 3,906,098 | 9/1975 | Barlow et al. | 71/92 X |

FOREIGN PATENT DOCUMENTS

| | | | |
|---|---|---|---|
| 285,241 | 10/1970 | Austria | 71/92 |
| 1,351,032 | 4/1974 | United Kingdom | 71/92 |
| 1,290,662 | 9/1972 | United Kingdom | 71/92 |

OTHER PUBLICATIONS

Toman et al., Chem. Abst., vol. 77 (1972), 57608y.
Greulach, Chem. Abst., vol. 55 (1961), 22692b.
Weed Control, 1961, John Wiley & Sons, Inc., p. 22.
Kurashi, Chem. Abst., vol. 54 (1960), 4781f.

*Primary Examiner*—Lewis Gotts
*Assistant Examiner*—Catherine L. Mills
*Attorney, Agent, or Firm*—Bernard J. Burns; George W. F. Simmons; William E. Lambert, III

[57] ABSTRACT

This invention relates to the selective herbicidal activity of fluoroaminopyridazines. In particular, these compounds exhibit preemergence and postemergence herbicidal activity on many of the major weeds including perennial weeds such as nutsedge and quackgrass. These compounds are particularly effective in selectively controlling weeds in agronomic crops.

7 Claims, No Drawings mulations or solutions. For example, the fluoroaminopyridazines can be formulated as wettable powders, emulsifiable concentrates, dusts, granular formulations, aerosols, or flowable emulsion concentrates. In such formulations, the compound is extended with a liquid or solid carrier and, when desired, suitable surfactants are incorporated.

It may be desirable in some applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The herbicides of this invention can be dissolved in any appropriate solvent. Examples of solvents which are useful in the practice of the invention include alcohols, ketones, aromatic hydrocarbons, dimethylformamide, dioxane, dimethyl sulfoxide, and the like. Mixtures of these solvents can also be used. The concentration of the solution can vary from about 2% to about 98% by weight of the active ingredient with a preferred range being about 25% to about 75%.

For the preparation of emulsifiable concentrates, the fluoroaminopyridazines can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersions in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 25% by weight and in flowable emulsion concentrates, this can be as high as about 75%.

Wettable powders suitable for spraying, can be prepared by admixing the active compounds of this invention with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, and preferably about 40% to 75%. A dispersing agent can constitute about 3% by weight of the composition, and a wetting agent can constitute from about 0.1% to about 5% of the composition.

Dusts can be prepared by mixing the compound of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% by weight of the active ingredient are commonly made and are subsequently diluted to about 1% to 10% as a use concentration.

Granular formulations can be prepared by impregnating a solid such as granular fuller's earth, vermiculite, ground corn cobs, seed hulls, including bran or other grain hulls, or similar material. A solution of fluoroaminopyridazine in a volatile organic solvent can be sprayed or mixed with the granular solid and the solvent then removed by evaporation. The granular material can have any suitable size, with a preferable size range of 16 to 60 mesh. The fluoroaminopyridazine will usually comprise about 2 to 15% by weight of the granular formulation.

The herbicide of the invention can also be mixed with fertilizers or fertilizing materials before application. In one type of solid fertilizing composition in which the fluoroaminopyridazines can be used, particles of a fertilizer or fertilizing ingredients, such as ammonium sulfate, ammonium nitrate, or ammonium phosphate, can be coated with the herbicide. The fluoroaminopyridazine and solid fertilizing material can also be admixed in mixing or blending equipment, or can be incorporated with fertilizers in granular formulations. Any relative proportion of herbicide and fertilizer can be used which is suitable for the crops and weeds to be treated. The herbicide will commonly be from about 5% to about 25% by weight of the fertilizing composition. These compositions provide fertilizing materials which promote the rapid growth of desired plants, and at the same time control the growth of undesired plants.

When used as a preemergence herbicide, fluoroaminopyridazines can be applied to the growth medium before the emergence of the weeds to be controlled by pre-plant soil incorporated application, by surface applications, or by any other convenient technique.

The fluoroaminopyridazine can be applied as a preemergence or postemergence herbicidal spray by methods commonly employed, such as conventional high-gallonge hydraulic sprays, low gallonage sprays, air-blast spray, aerial sprays and dusts. For low volume applications a solution of the compound is usually used. The dilution and rate of application will usually depend upon such factors as the type of equipment employed, the method of application, the area to be treated, and the weeds to be controlled, and the like.

For some applications, it may be desirable to add one or more other herbicides along with the fluoroaminopyridazine. Examples of other herbicides which can be incorporated to provide additional advantages and improve effectiveness include:

CARBOXYLIC ACIDS AND DERIVATIVES 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy) propionic acid and its salts and ester and ester 4-(2,4-dichlorophenoxy) butyric acid and its salts and esters
4-(2-methyl-4-chlorophenoxy) butyric acid and its salts
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts

CARBAMIC ACID DERIVATIVES ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroally N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

PHENOLS dinitro-o-(sec-butyl)phenol and its salts
pentachlorophenol and its salts

SUBSTITUTED UREAS 3-(3,4-dichlorophenyl)-1,1-dimethylurea
3-(4-chlorophenyl)-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea dichloral urea

SUBSTITUTED TRIAZINES 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine 2-methoxy-4-ethylamino-6-isopropylamion-s-triazine
2-methylmercapto-4-(2-methoxyethylamino)-6-isopropylamino-s-triazine
4-amino-6-terbutyl-3-(methylthio)-as-triazine-5(4H)-one

DIPHENYL ETHER DERIVATIVES 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether

ANILIDES

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-a,a-dimethylvaleramide

URACILS 5-bromo-3-s-butyl-6-methyluracil
5-bromo-3-cyclohexyl-1,6-dimethyluracil
5-bromo-3-isopropyl-6-methyluracil
3-tert-butyl-5-chloro-6-methyluracil

NITRILES 2,6-dichlorobenzonitrile
diphenylacetonitrile
3,5-dibromo-4-hydroxybenzonitrile
3,5-diiodo-4-hydroxybenzonitrile

OTHER ORGANIC HERBICIDES 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-a,a-diphenylacetamide
N,N-di(n-propyl)-2,6-dinitro-4-trifluoromethylaniline This invention as disclosed above relates to the use of fluoroaminopyridazines as selective preemergence and postemergence herbicides on agronomic crops. It is furthermore intended that the various other methods and variations of application which suggest themselves to one skilled in the art of agriculture and horticulture be also included in this invention.

We claim:
1. A method of controlling weeds which comprises applying to the area in which the weeds are to be controlled a herbicidally effective amount of a compound of the formula

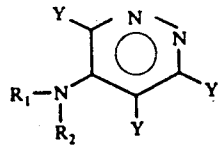

wherein Y is chlorine or fluorine; $R_1$ and $R_2$ are independently hydrogen, ethyl or chloroacetyl.

2. A method of controlling weeds according to claim 1 wherein Y is fluorine and $R_1$ and $R_2$ are both hydrogen.

3. A method of controlling weeds in agronomic crops which comprises applying to the surface of the growth medium, prior to the emergence of weeds from the growth medium, a compound according to claim 1, in an amount sufficient to control the growth of the weeds.

4. A method of claim 1 wherein the herbicidally effective amount is from 0.5 to 20 pounds per acre.

5. A method of claim 1 wherein the herbicidally effective amount is from 1 to 8 pounds per acre.

6. A method of claim 2 wherein the compound is applied at a rate of about 0.5 to about 20 pounds per acre.

7. A method of claim 2 wherein the compound is applied at a rate of about 1 to 8 pounds per acre.